(12) United States Patent
Lee et al.

(10) Patent No.: US 12,116,569 B2
(45) Date of Patent: Oct. 15, 2024

(54) VORTEX GENERATOR FOR AGITATION OF FLUIDS DURING SAMPLE PREPARATION

(71) Applicant: Siemens Healthcare Diagnostics Inc., Tarrytown, NY (US)

(72) Inventors: Alex Hofai Lee, Fremont, CA (US); Daniel Chu, Hercules, CA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 18/328,085

(22) Filed: Jun. 2, 2023

(65) Prior Publication Data

US 2023/0313172 A1    Oct. 5, 2023

Related U.S. Application Data

(63) Continuation of application No. 17/759,417, filed as application No. PCT/US2021/070106 on Feb. 1, 2021, now Pat. No. 11,680,258.
(Continued)

(51) Int. Cl.
  *B01F 31/441* (2022.01)
  *B01F 31/44* (2022.01)
  (Continued)

(52) U.S. Cl.
  CPC ........ *C12N 15/1013* (2013.01); *B01F 31/441* (2022.01); *B01F 31/449* (2022.01);
  (Continued)

(58) Field of Classification Search
  CPC .. C12N 15/1003; B01F 33/452; B01F 33/813; B01F 31/449; B01F 31/441;
  (Continued)

(56) References Cited

U.S. PATENT DOCUMENTS 11,680,258 B2 *  6/2023  Lee ................... B03C 1/288
                                                  422/527
2003/0203491 A1  10/2003  Andrevski et al.
(Continued)

FOREIGN PATENT DOCUMENTS

| CN | 106591297 | 4/2017 |
| CN | 110270257 | 9/2019 |
| EP | 1516920   | 3/2005 |

OTHER PUBLICATIONS

International Search Report for PCT/US2021/070106 dated Apr. 9, 2021.
(Continued)

*Primary Examiner* — Brian J. Sines

(57) ABSTRACT

An apparatus, vortex generator assembly and method for automated cell lysis and nucleic acid purification and processing. The vortex generator assembly includes sample holder having a lysis well, at least one wash well, and an elution well. The vortex generator assembly also includes a sample holder cover having a plurality of vibration rods for creating a vortex in the wells of the sample holder. The apparatus includes motor operating a rotating cam to cause the vibration rods to vibrate and create the vortex in a well holding fluid and magnetic beads, wherein the vortexing speed is sufficient to overcome the magnetic attraction between the beads and disperse the beads in solution, to collect nucleic acids such as DNA.

20 Claims, 8 Drawing Sheets

Related U.S. Application Data

(60) Provisional application No. 62/989,285, filed on Mar. 13, 2020.

(51) Int. Cl.
| | |
|---|---|
| *B01F 33/452* | (2022.01) |
| *B01F 33/81* | (2022.01) |
| *B01F 101/23* | (2022.01) |
| *B01L 3/00* | (2006.01) |
| *B03C 1/01* | (2006.01) |
| *B03C 1/28* | (2006.01) |
| *C12N 15/10* | (2006.01) |

(52) U.S. Cl.
CPC .......... *B01F 33/452* (2022.01); *B01F 33/813* (2022.01); *B01L 3/5085* (2013.01); *B03C 1/01* (2013.01); *B03C 1/288* (2013.01); *B01F 2101/23* (2022.01); *B01L 2200/0647* (2013.01); *B03C 2201/18* (2013.01); *B03C 2201/26* (2013.01)

(58) Field of Classification Search
CPC .......... B01F 2101/23; B01F 2200/0647; B01L 3/5085; B03C 2201/26
See application file for complete search history.

(56) References Cited

U.S. PATENT DOCUMENTS

| | | |
|---|---|---|
| 2011/0091879 A1 | 4/2011 | Hillebrand et al. |
| 2011/0306109 A1 | 12/2011 | Kelso et al. |
| 2013/0130369 A1 | 5/2013 | Wilson et al. |
| 2015/0352512 A1 | 12/2015 | Whalen et al. |

OTHER PUBLICATIONS

Yang Lei: "Preparation and application of magnetic silica modified with cationic on the surface as an example", p. 1-49, Sep. 15, 2010. (see English abstract).

* cited by examiner

VORTEX GENERATOR FOR AGITATION OF FLUIDS DURING SAMPLE PREPARATION

CROSS-REFERENCE TO RELATED APPLICATIONS

This is a continuation application claiming priority from of U.S. patent application Ser. No. 17/759,417 filed on 25 Jul. 2022 which is a 35 U.S.C. 371 national application of international application no. PCT/US2021/070106 filed 1 Feb. 2021, which claims priority of U.S. Provisional application No. 62/989,285 filed 13 Mar. 2020, the contents of which are fully incorporated herein by reference.

FIELD OF THE DISCLOSURE

The disclosure herein relates generally to the field of cell lysing and nucleic acid purification and isolation. More particularly, the present disclosure relates to a multi-well sample holder and cover with vibration rods having utility in the field of nucleic acid extraction in molecular diagnostics.

BACKGROUND

In some protocols for cell lysis and nucleic acid isolation using magnetic beads, a sample is moved by a pipette system to a well within a multi-well plate, or sample holder, along with a cell lysis buffer and a quantity of magnetic beads. The beads are functionalized, for example with silica surfaces, to allow selective binding of nucleic acid molecules such as DNA. A succession of mixing by external vibration, magnetic bead separation, supernatant aspiration, and dilution/washing steps are repeated. These may be performed in the same well, or the magnetic beads may be moved from well to well for various steps. Heating of one or more of the wells of the sample holder may also be employed to facilitate lysis and/or binding. The sample transfer, washing, and elution steps require separate aspiration and dispensing tips to avoid cross-contamination.

Using magnetic beads in a sample fluid contained within a well to capture and extract nucleic acids from the specimens requires magnetic devices as the tools for accomplishment of workflow. Magnets may be used inside a probe that is inserted into the well to collect the magnetic beads prior to transfer to another well. Magnets may also be used outside the well to manipulate magnetic beads. Manipulating magnets in a fluid by magnetic movement and shaking the well itself, as well as by vortex mixing, are also known.

Effective mixing is critical in cell lysis and washing steps for sample preparation to ensure that an adequate amount and quality of nucleic acids are extracted from the sample. Vortex mixing is one of the most effective mixing techniques, but to generate a vortex in a small volume is difficult without a bulky setup.

In the field of molecular diagnostics, there is a need for an efficient and cost-effective system and method for lysing cells and purifying samples for amplicon detection. There is further a need for mixing magnetic beads in multiple processing steps that minimizes liquid handling, contamination and reagent carryover.

SUMMARY

A system and method for extracting nucleic acids from specimens using both magnetic and mechanical oscillation to enhance the speed and efficiency of mixing is disclosed. Vortex generation in a multi-well sample holder is performed by vibration rods. Vibration rods attached to cantilevers and inserted into wells may generate a high-speed vortex in a very confined space with small volume of fluid. The driving unit or oscillation source is a rotating cam (or non-round profile action such as rotating spur gear) that interacts with tabs on the cantilevers. In embodiments, a vibration rod method does not vibrate the containers or tubes, but simply transfers the oscillation energy directly to the fluid with the vibration of rods so that a vortex is generated in a very small confined space at high speed. Also, the magnetic beads for target nucleic acid extraction may be agitated physically with the rod vibration, leading to less aggregation in real biological samples, i.e. whole blood. Magnetic beads and associated nucleic acid molecules may be moved between wells using a magnetic that is external to the sample holder.

A sample holder and cover may be assembled easily and flexibly. The sample holder is an array of wells that hold fluid and magnetic beads during processing and moving from well to well. The sample holder cover is an array of vibration rods corresponding to some or all of the wells.

BRIEF DESCRIPTION OF THE DRAWINGS

Illustrative embodiments of the disclosed technology are described in detail below with reference to the attached drawing figures, which are incorporated by reference herein and wherein.

DETAILED DESCRIPTION

Disclosed herein is an apparatus for extracting nucleic acids such as DNA molecules from biological samples. Use of the presently disclosed and described apparatus enables simplified, easy, and reliable mixing and transfer of magnetic beads between wells in a fashion particularly suitable to automated sample preparation techniques. In embodiments, magnetic beads may be magnetic micron- or nano-particles with a surface modification which binds target nucleic acids released during a sample preparation process of biological specimens. In the systems and methods described herein, a magnetic field is the only driving force for sample and/or magnetic bead handling and transportation. Liquid handling is eliminated resulting in minimization of cross-contamination and liquid carryover. Magnetic beads are transferred from well to well within a consumable sample holder using a single module to drag beads along an internal plastic surface of the consumable, providing improved cleaning and drying. In further embodiments, the consumable sample holder is self-contained, cleaning of other components of the system is not required, thereby minimizing biohazard exposure.

Figure 1:
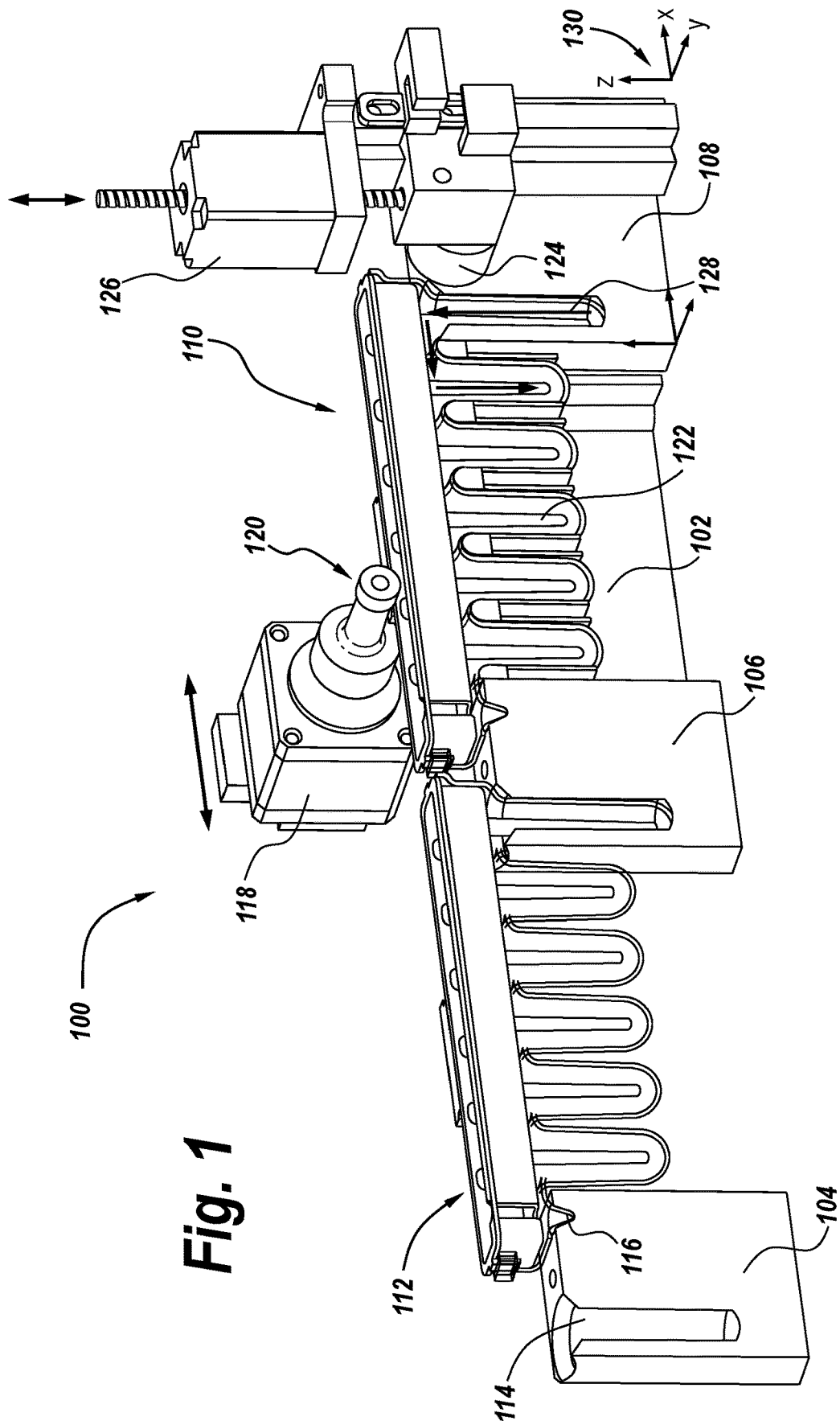
FIG. 1 is a perspective view of a sample lysis and nucleic acid extraction apparatus according to the present disclosure.

FIG. 1 illustrates an exemplary embodiment of an apparatus 100 for extracting nucleic acids from specimens according to the present disclosure. The apparatus 100 is comprised of a base, indicated generally at 102, 104, 106 and 108. Base 102 is used to retain vortex generator assembly 110 in position together with heating blocks 106 and 108. In the embodiment of FIG. 1, a second vortex generator assembly 112 is retained in position by heating block 106 and heating block 104. Heating blocks 104, 106 and 108 each include a cavity 114 for receiving a lysis well and a cavity 116 for receiving an elution well of vortex generator assemblies 110 or 112, discussed in more detail with reference to FIG. 2. Cavity 114 of heating block 104 is empty as shown in FIG. 1, but may receive a lysis well of a third vortex generator assembly. Any number of vortex generator assemblies may be connected in sequence, within the range of motion of the stepper motors described below.

Apparatus 100 further includes a stepper motor 118. Selective actuation of motor 118 causes rotating cam 120 to spin and translate rotary motion into linear motion of vibration rod 122. In an exemplary embodiment, the rotating cam spins at approximately 5 Hz to 20 kHz. The contact angle between rotating cam 120 and a vibration rod 122 may also be finely adjusted to optimize the vortex within wells. A horizontal actuator (not shown) moves motor 118 along an x-axis as defined by axes 130, repositioning motor 118 along vortex generator assemblies 110 and 112 during sample processing. Motor 118 may also include a vertical actuator for moving motor 118 along the z-axis.

In addition, the apparatus 100 may include an magnet 124 external to vortex generator assemblies 110 and 112 that may be selectively translated by stepper motor 126 in all three of x, y and z axes. Magnet 124 may be moved along vortex generator assemblies 110, 112 along the x-axis, closer and farther away from a side wall of a vessel along the y-axis as defined by axes 130, in order to attract and release, respectively, magnetic beads disposed within a vessel, and vertically along the z-axis, as will be discussed subsequently. Operation and oscillation of motors 118 and 126 may be synchronized or individual for optimization and different operating modes.

Figure 2:
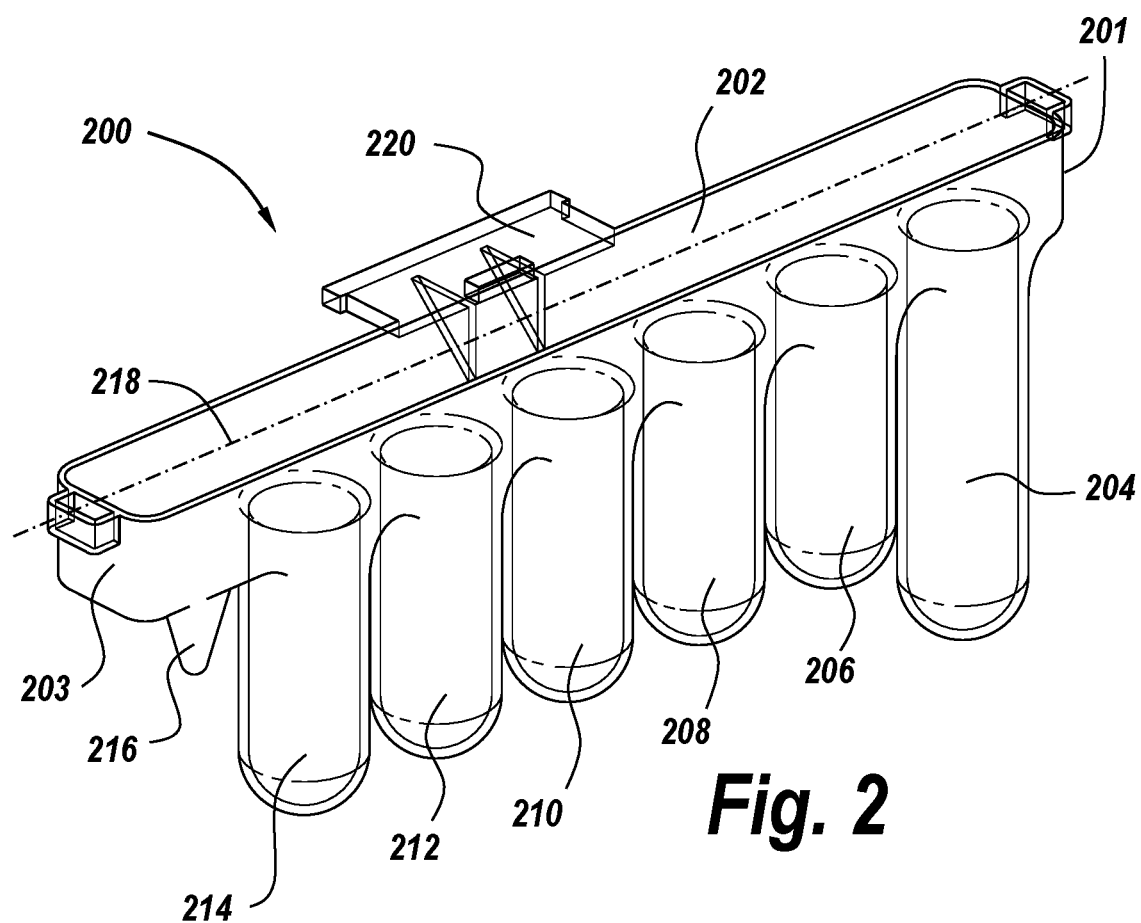
FIG. 2 is a perspective view of a sample holder of a vortex generator assembly according to the present disclosure.

An embodiment of vortex generator assembly 110, 112 is shown in FIGS. 2-4. Vortex generator assembly may also be referred to as a multi-well plate, or sample holder, for use in cell lysing and nucleotide purification together with a sample holder cover. FIG. 2 illustrates an embodiment of a sample holder 200 having a body member and a plurality of wells extending in a downwardly direction from the floor of the body member, according to the present disclosure. In this embodiment, the body member is a channel 202 and the process wells include a lysis well 204, wash wells 206, 208, 210, 212, 214, and elution well 216. Channel 202 may help inhibit the unintended flow of working fluid off sample holder 200.

Lysis well 204 is disposed at a first end 201 of the sample holder 200 while the wash wells are disposed intermediate the first end and an opposite second end 203 where elution well 216 is located. Each well extends in a substantially orthogonal direction from the floor of the channel 202 and has an interior volume communicating with the channel via an aperture in the channel floor. The illustrated apertures are circular and coplanar with the floor surface, although embodiments of differing shapes and orientations are also contemplated. The apertures are also substantially colinear along the floor surface and are centered about a longitudinal axis 218 of symmetry of the sample holder.

In order to optimize vortexing, lysis well 204 may have a larger volume than the wash wells in order to provide sufficient space for the biological sample, lysis buffer, and magnetic beads. Conversely, elution well 216 may have a smaller volume than the wash wells in order to minimize dilution of the final nucleic acid product and may be characterized by a conical cross-section to facilitate removal of the product with a pipettor or other devices for transferring fluids.

Lysis well 204 of sample holder 200 may be subjected to heating, depending upon the characteristics of the lysis process implemented therewith. For example, the outer surface of the lower extent of the lysis well 204 may be configured to be received within a heater external to the unitary structure. Such a heater may be a heating block 108 placed beneath the holder, receiving the outer surface of the lower extent of lysis well 204 within cavity 114 and heating lysis well 204 for a required or desired time period. Similarly, the elution well 216 of the sample holder 200 may be heated with another heater external to the unitary structure, such as cavity 116 of heating block 106, depending upon the elution process implemented therewith. Heating blocks may provide temperatures up to approximately 120° C.

In one embodiment, the wells are pre-filled with appropriate buffers and other components and then sealed off, for example with a peel-away layer that is removed at the time of use. In another embodiment, the wells each have a tapered lower extent. This enables multiple sample holders to be vertically stacked, whereby the outer surface of a lysis well of a first holder is received within the lysis well of a lower, second holder. Similarly, the outer surfaces of the wash wells of the first holder are each received within a respective wash well of the lower, second holder.

Sample holder 200 may be provided with retention features, such as tab 220 projecting from the upper rim of channel 202 or other lateral projections extending from the sample holder on either side of sample holder 200. During processes such as heating and vortexing, when external devices move relative to sample holder 200, the retention features may be selectively engaged by external releasable gripping mechanisms, thereby maintaining the multi-well plate in a fixed position relative to the external devices. The retention features may also be of use during the introduction of samples, buffers, beads or other components in the wells or eluted product retrieval as a pipetting system presses down on the inner surface of the elution well 216. Alternatively, sample holder 200 and associated heating blocks and support structures, i.e., base 102, may be configured for lateral, horizontal translation relative to the motors 118 and 126, thus obviating the need for enabling horizontal translation of the rotor mixer and associated components.

In embodiments, sample holder 200 may handle a wide range of fluid quantities, from 1500 to 3 µL in a single piece because the sample preparation procedure of biological specimens may vary widely among different matrices from whole blood, plasma, serum, stool, urine, sputum, swabs. Sample holder 200 provides flexibility to cover all those but not limited to the aforementioned specimen types. In embodiments, sample holder 200 may include seven compartments in one molded piece of polymer selected from, for example, polypropylene, polyethylene, polyethylene terephthalate (PET), cyclic olefin copolymer, polycarbonate or polyacrylates.

In embodiments, a volume size of wells in sample holder 200 ranges from 1.5 to 2.0 mL to 50 to 200 µL for different applications with different fill liquid. The compartments can be assigned to Lysis, Incubation, Washing, Drying and Extraction functions with different programming.

Figure 3A:
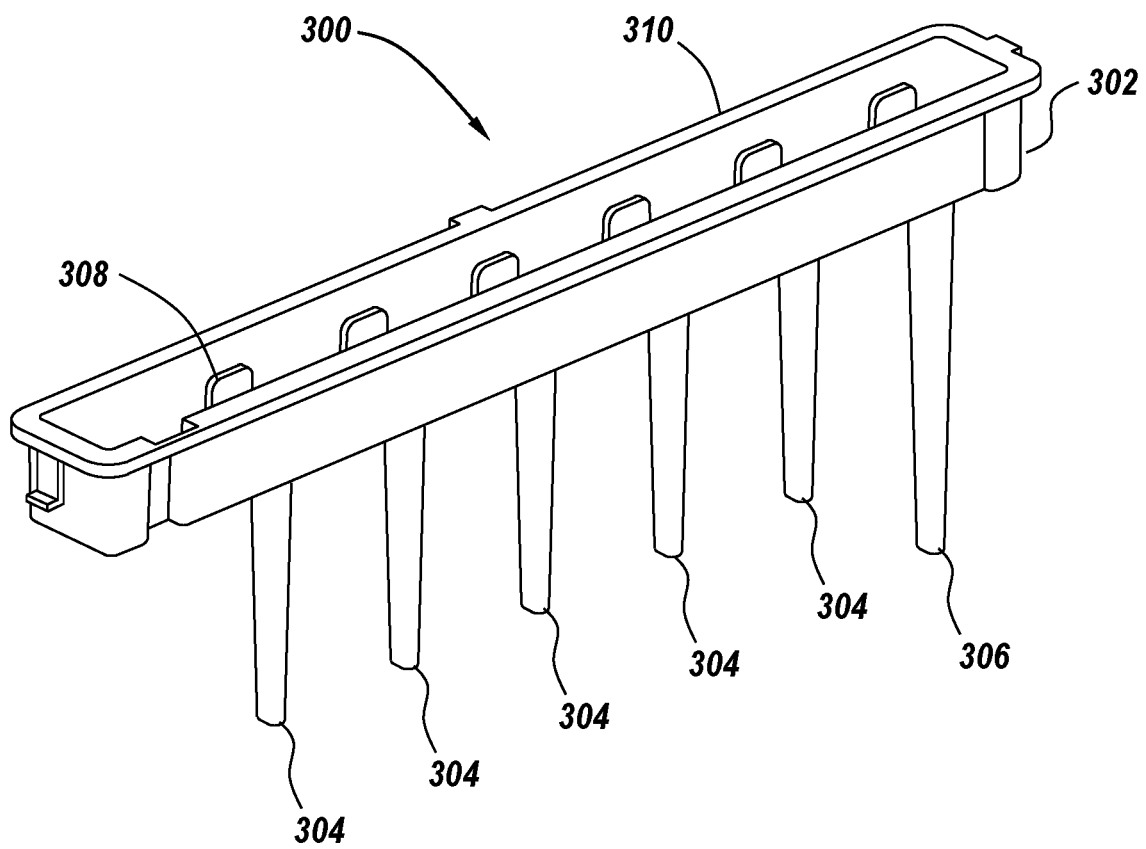
FIG. 3A is a perspective view of a sample holder cover of a vortex generator assembly according to the present disclosure.

FIG. 3A illustrates a sample holder cover 300 for use with sample holder 200 of FIG. 2, in an embodiment. Sample holder cover 300 includes a base member 302 sized and shaped for insertion into channel 202. Base member 302 may be retained within channel 202 in several ways. It may be sized to fit snugly into channel 202 with a friction fit, it may snap into channel 202 or it may be retained with channel 202 using one or more clips. In embodiments, base member 302 includes a plurality of vibration rods 304, 306 extending in a downwardly direction from base member 302. As shown in FIG. 3A, vibration rods 304 correspond to wash wells 206, 208, 210, 212 and 214 of sample holder 200, however, any number of vibration rods may be provided. Vibration rod 306 is intended for insertion into lysis well 204 and thus, is proportionally bigger than vibration rods 304 in the same way that lysis well 204 is proportionally larger than wash wells 206-214. Vibration rods 304, 306 are positioned on base member 302 so as to be generally centered in the interior volume of a respective well when base member 302 is inserted into channel 202.

A tab, indicated at 308, corresponds to each vibration rod 304, 306 and is used to cause vibration rods 304, 306 to vibrate in conjunction with rotating cam 120 of FIG. 1. Tabs 308 extend from base member 302 in an upwardly direction relative to vibration rods 304, 306. Tabs 308 also extend above rim 310 of base member 302 for engagement with rotating cam 120. In embodiments, tabs 308 may be recessed below rim 310 and rotating cam 120 may be positioned to extend down into cover 300 slightly to engage with tabs 308.

Figure 3B:
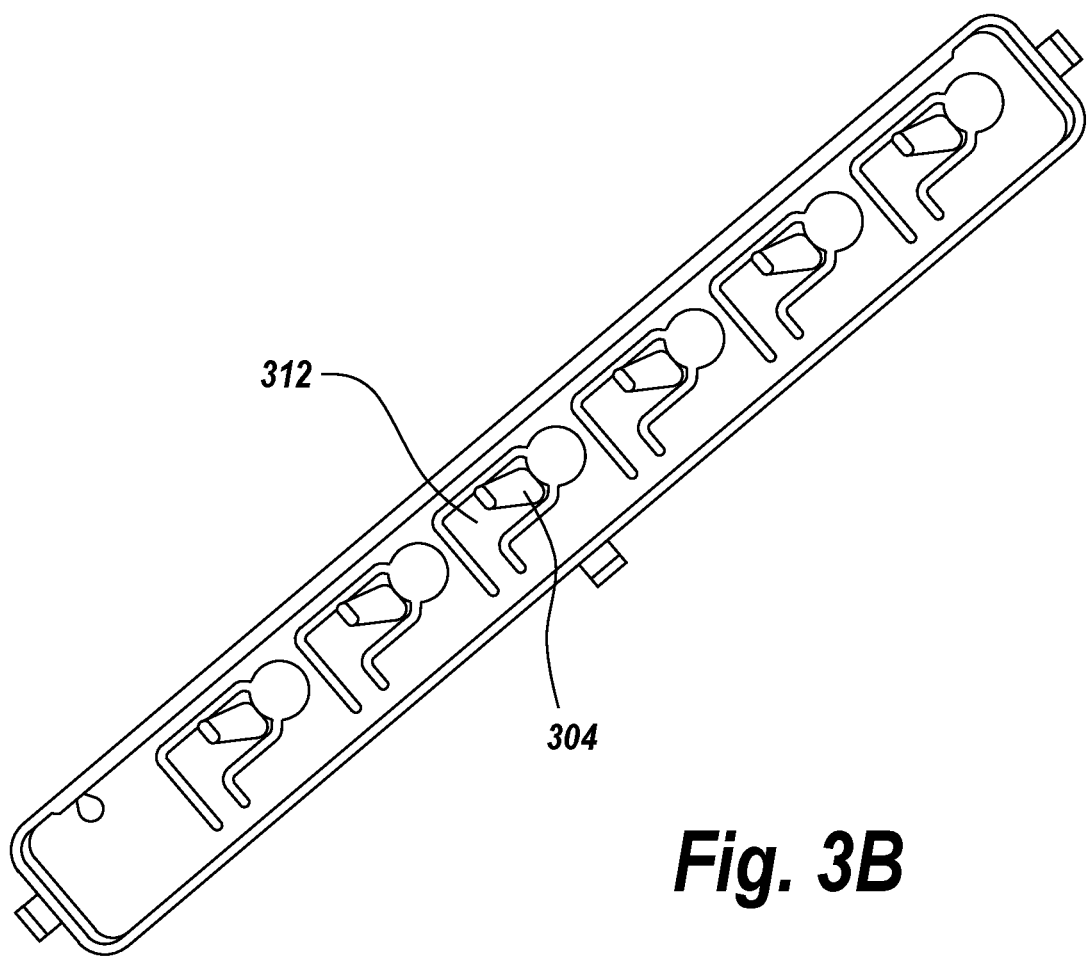
FIG. 3B is a bottom perspective view of the sample holder cover of FIG. 3A according to the present disclosure.

FIG. 3B shows a bottom perspective view of sample holder cover 300. Each vibration rod 304 is attached to base member 302 at one end of a cantilever 312. A tab 308 is located on the opposite side of each cantilever 312 as shown in FIG. 3A. Cantilever 312 allows vibration rod 304 to be vibrated at a selectable speed and duration through control of rotating cam 120.

Figure 4A:
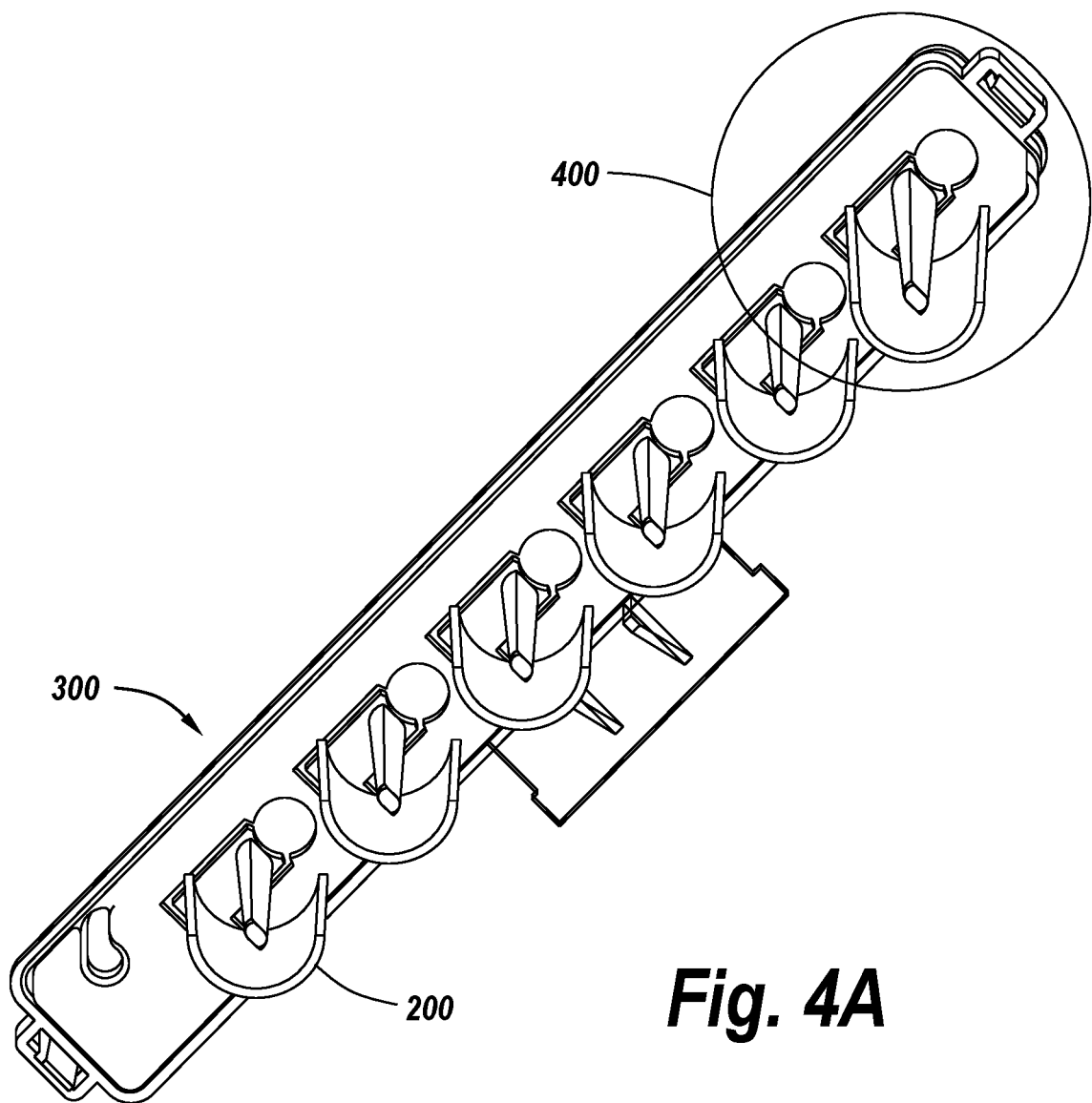
FIG. 4A is a bottom perspective view of a vortex generator assembly according the present disclosure.

FIG. 4A shows a bottom perspective view of a portion of sample holder 200 and sample holder cover 300 combined to form a vortex generator assembly 110, 112. A more detailed view 400 is shown in FIG. 4B.

Figure 4B:
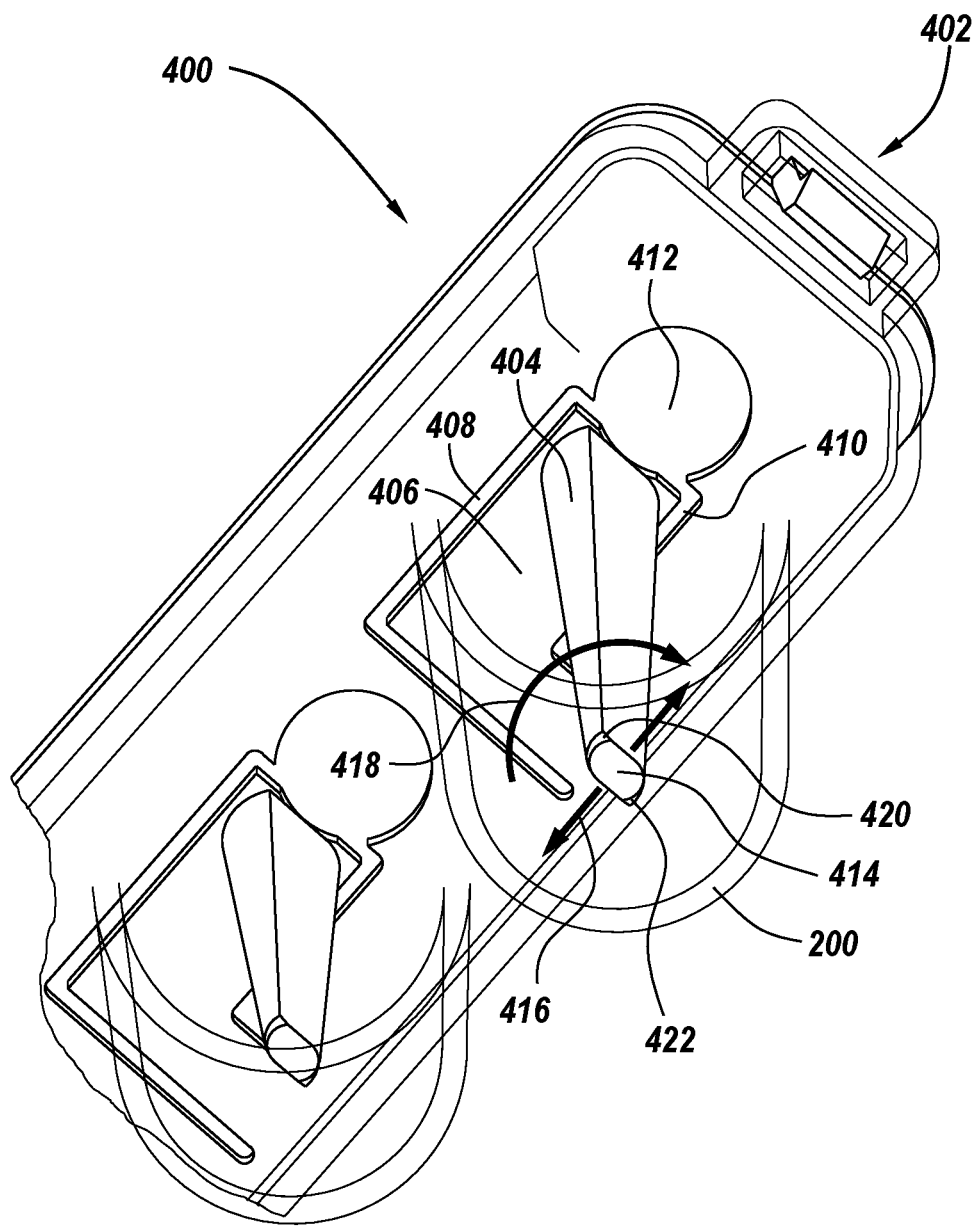
FIG. 4B is a detailed view of a portion of FIG. 4A.

FIG. 4B shows a close-up bottom view of a vortex generator assembly 110. Sample holder 200 is shown transparently so details of sample holder cover 300 may be illustrated. Sample holder cover 300 has been inserted into sample holder and held in place using snapping mechanism 402. Mechanism 402 is depicted as a tab on sample holder cover 300 that is inserted and retained in a slot on sample holder 200, but other mechanisms and designs may be used. Other mechanisms for retaining the sample holder cover in the sample holder are also contemplated.

Vibration rod 404 is attached to cantilever 406, which has been formed from a floor of base member 302 by cutout areas 408 and 410. In embodiments, cutout area 412 allows the oscillation/vibration from rotating cam 120 through tab 308 to vibration rod 404 to be performed with less energy loss. It may also provide access for liquid dispensing and aspiration. Cutout areas 408, 410 and 412 create cantilever 406 which is able to oscillate up and down in response to engagement of rotating cam 120 with tab 308. As explained above with reference to FIGS. 1 and 3, the oscillation driving force from spinning cam 120 motion engages with tab 308 on the opposite side of cantilever 406 (not visible in this view) which leads to vibration at the rod end 414, as shown by motion arrows 416. The design of vibration rod 404 causes vibration energy to be directly transferred to fluid in sample holder 200, creating a vortex 418 in fluid in sample holder 200. Further, the dimension of the rod allows generation of vortex in very confined and small volume.

Rod 404 has an asymmetric cross section along its length extending from the base member to its tip, as shown at rod end 414. Flanges 420 and 422 on either side of rod end 414 enhance the creation of vortex 418. Although a representative cross-section and flange arrangement has been shown, this is for purposes of illustration and other designs for vibration rod 404 are contemplated. The shape and dimension of vibration rods may be customized for different fluids and methods of mixing without requiring changes to the overall system.

Figure 5:
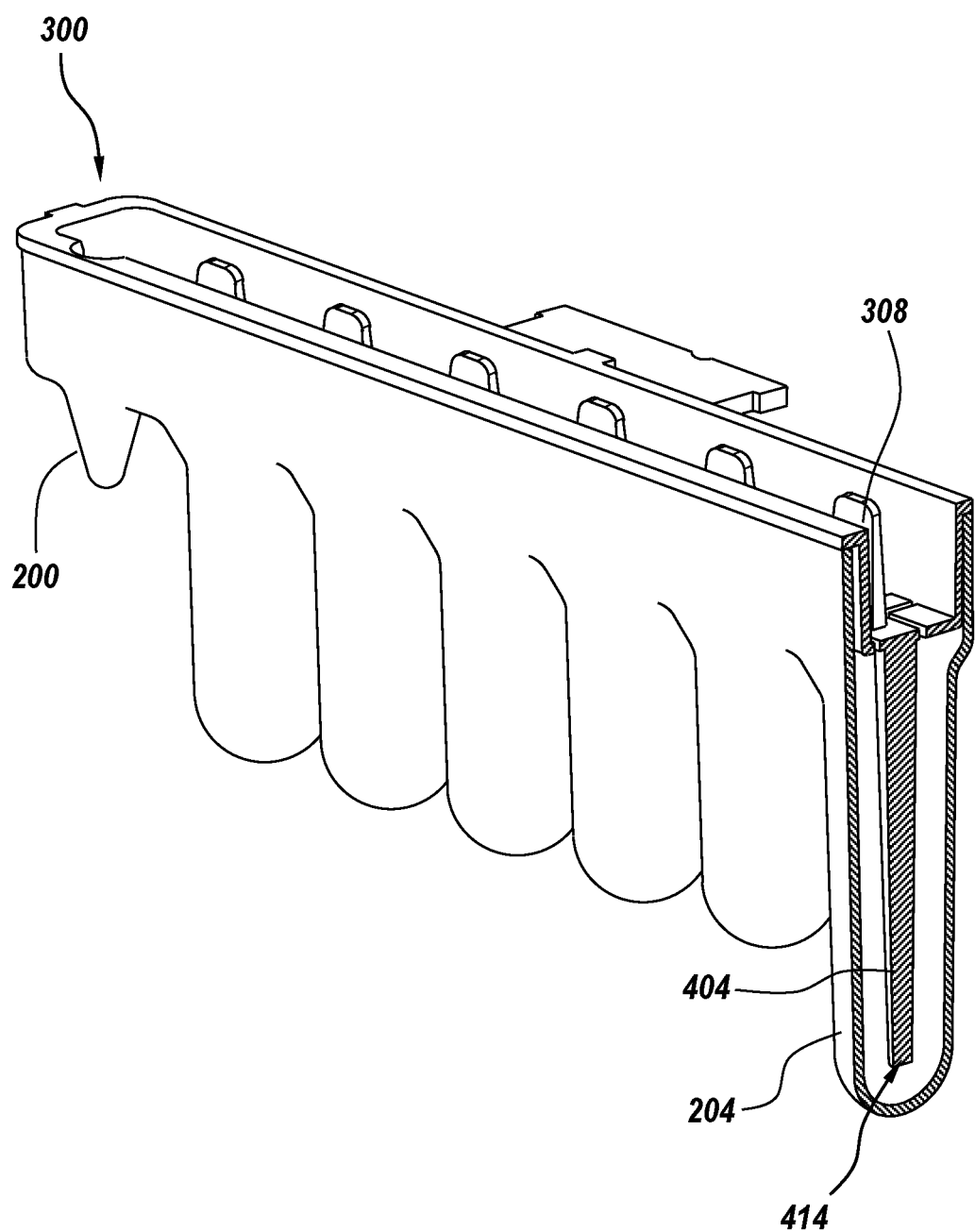
FIG. 5 is a cross-sectional view of a vortex generator assembly, according to the present disclosure.

FIG. 5 shows a vortex generator assembly with sample holder cover 300 is inserted in sample holder 200. Lysis well 204 is shown in cross-section to illustrate the positions of vibration rod 404 and tab 308. Rotating cam 120 engages with tab 308 to impart a vibration to vibration rod 404. As stepper motor 118 moves between adjacent tabs, rotating cam 120 engages with adjacent vibration rods. Because of the cantilever attachment of vibration rod 404, the vibration movement of vibration rod 404 will be largest at rod end 414. This may provide improved fluid handling and less aggregation in some types of sample fluid. Further customization of vortex mixing may be provided by controlling the spin rate and length of rotation cam 120.

Referring to FIG. 1, operation of apparatus 100 will now be described. Stepper motor 118 causes rotating cam 120 to spin and translate rotary motion into linear motion of vibration rod 122. A horizontal actuator (not shown), repositions motor 118 along vortex generator assemblies 110 and 112 during sample processing. Stepper motor 126 includes actuators for moving magnet 124 in three directions: horizontally along the x-axis to reposition magnet 124 along vortex generator assembly 110, horizontally along the y-axis from positions closer to and farther away from assembly 110, and vertically along the z-axis. Motors 118 and 126 may be independently controlled so that both magnetic and mechanical oscillation may be used to mix and manipulate magnetic beads and fluid in a sample holder.

Figure 6:
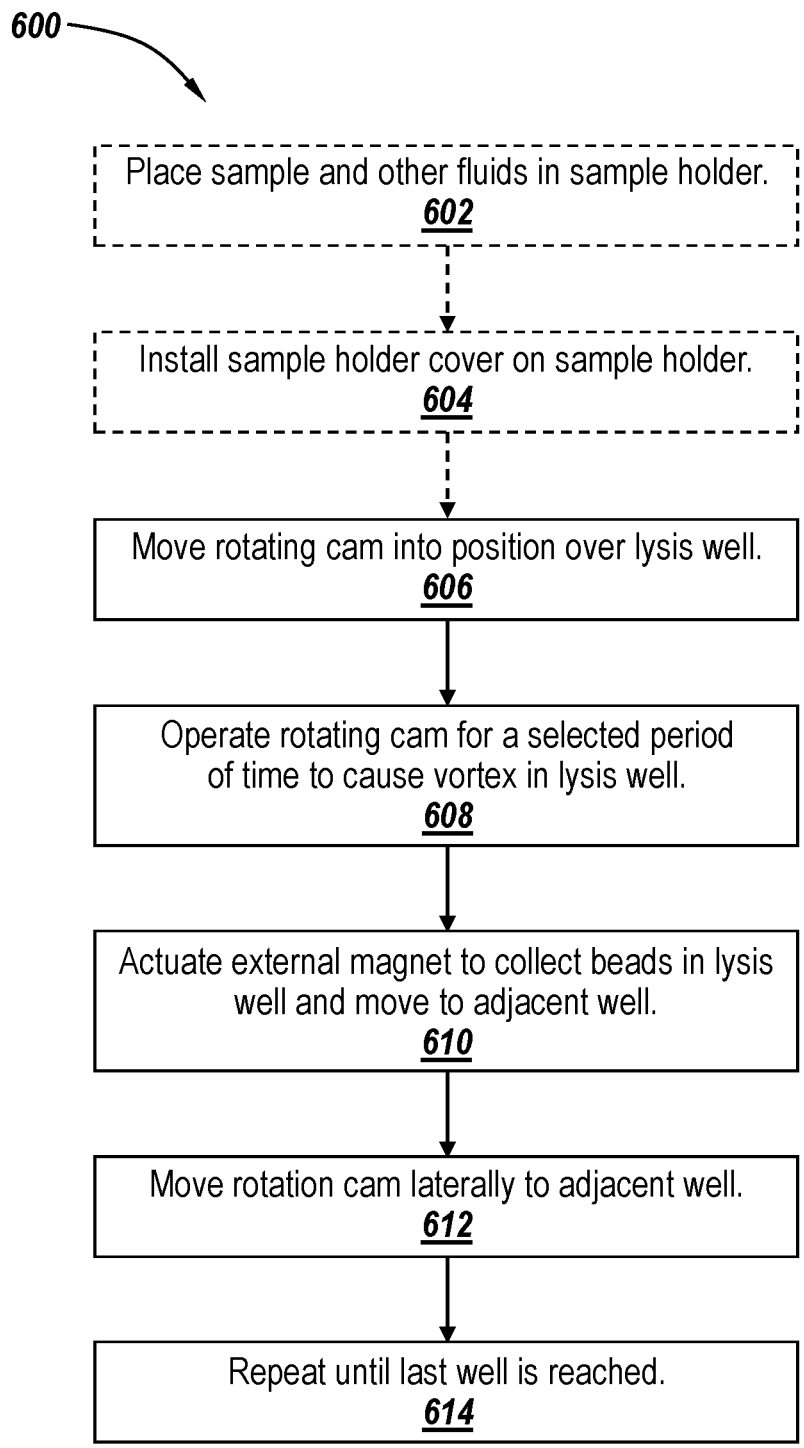
FIG. 6 is a flowchart illustrating a method of using a sample lysis and nucleic acid extraction apparatus with a vortex generator assembly, according to the present disclosure.

FIG. 6 is a flowchart of a method of operating the components of apparatus 100. Not all steps need be practiced in the order described below, nor be utilized at all, depending upon the embodiment.

Step 602 includes placing a sample, magnetic beads and other fluids or buffers in sample holder 200. In an example of step 602, one or more wash buffers are loaded into the wash wells 206, 208, 210, 212, 214, an elution buffer is loaded into elution well 216, and lysis buffer is loaded into the lysis well 204. Magnetic beads are also introduced in the lysis well 204. In one example, the material of the beads may be optimized for genomic DNA extraction from blood samples, but its composition may vary to suit other types of bodily fluids or tissues or for extracting other types of nucleic acids such as RNA. A biological sample is then loaded into the lysis well, yielding a lysis mixture ready for vortexing. Typical samples include blood, sputum, hair, and other bodily fluids and tissues, optionally pretreated for example by freezing, homogenizing, or grinding. Those of skill in the art will recognize that the choice of buffers and other reactants may vary according to the type of sample and beads to provide optimal conditions for nucleic acid extraction. While this illustrated process depicts a certain order of loading the lysis well to form the lysis mixture, other orders may be employed, such as disposing the sample into the lysis well prior to adding the magnetic beads. In embodiments, sample holder 200 may be preloaded with fluids or they may be added with a pipette system, for example.

Step 604 includes installing a sample holder cover 300 on sample holder 200. In an example of step 604, sample holder cover 300 may be snapped or otherwise securely retained in sample holder 200.

Step 606 includes moving rotating cam 120 into position over a lysis well 204 of sample holder 200. In an example of step 606, rotating cam 120 is positioned so that it will make contact with a tab 308 of a vibration rod 306 inserted into lysis well 204.

Step 608 includes operating rotation cam 120 for a selected period of time to cause a vortex in lysis well 204. In an example of step 608, both a rotation speed and length of time for rotating are selectable depending on the sample being mixed and mixing may be performed either continuously or intermittently. For at least a portion of the vortexing step, the rotating cam 120 is spun at a rate sufficient to overcome attraction forces between magnetic beads, thereby freeing the beads to swirl about the lysis mixture and bind to nucleic acid molecules dispersed therein following cell lysis. In an exemplary embodiment, the rotating cam spins at approximately 5 Hz to 20 kHz. In embodiments, magnet 124 may also be moved along any of the x, y or z axes in coordination with rotating cam 120 to facilitate vortex generation and mixing.

Step 610 includes actuating magnet 124 to move magnetic beads and associated nucleic acids to an adjacent well. In an example of step 610, magnet 124 is moved by motor 126 into a position adjacent to a side wall of a lysis well 204 in order to attract magnetic beads disposed within the well. Then motor 126 is actuated to move magnet 124 along motions arrows 128, vertically to an aperture of lysis well 204, horizontally across a floor of channel 202 to an adjacent wash well 206, then vertically into down into wash well 206. Magnet 124 may then be moved horizontally along the y-axis to release magnetic beads into the wash fluid in well 206. In embodiments, the floor of channel 202 is lower than the floor of base member 302 of sample holder cover 300 so that magnetic beads may be moved from well to well in sample holder 200 without interference from the sample holder cover.

Step 612 includes moving rotating cam horizontally along the x-axis to tab 308 connected to vibration rod 304 inserted into wash well 206. In step 614, steps 608-612 are repeated until the last well of vortex generator assembly 110, 112 is reached. In each well of sample holder 200, a process similar to that executed within lysis well 204 may be carried out. After a desired number of washing steps have been completed, magnet 124 is actuated to move magnetic beads into elution well 216 of sample holder 200 where nucleic acids elute from the magnetic beads into the elution buffer.

As anticipated, the contents of the lysis well 204 may be heated prior to or during the illustrated step 608 of vortexing the contents of the lysis well. Following removal of the magnetic beads in step 610, liquid residues in the lysis well and the wash wells may be aspirated by a pipetting system and dispensed to a waste receptacle. In embodiments, this may be done by removing sample holder cover 300 or through cutout area 412 of FIG. 4B. Similarly, elution well 216 may undergo heating at any point prior to removal of the final nucleotide product solution.

Embodiments described above have several advantages. The system provides improved vortex generation in a confined and small volume with easily fined tuned speed and low-cost assembly of driving source. As the effective mixing is critical for the Sample Preparation for qPCR, this mixing invention can be lead to significant improvement of time, efficiency, throughput and quality of PCR assays. The vibration source is a simple motor connected to a cam shaft. This allows the flexibility of speed selection and cost saving. One driving source is good for driving vortex mixing in different positions.

Further, a vortex generator assembly with multiple vibration rods in an array has low production cost and it is easy to modify and optimize the vortex generation by slightly changing the shape and dimension of the rod. In embodiments, apparatus and methods used above may be incorporated in a high throughput liquid handling robot such that every well on a plate having, for example, 96, 192, 384 wells may be agitated at the same time. This may reduce the cost of multiple batches using disposable pipette tips for liquid up-down handling, with better and faster mixing. Only a single source of mechanical oscillation is needed to multiple throughputs. In another embodiment, multiple sources of mechanical oscillation may be used.

In embodiments, a system and method as described herein may be used with or without magnetic beads. High speed processing with minimal wait time operation may be accomplished by programing the synchronized motions of magnetic and mechanical driving units. Heating elements may be used in conjunction with mixing, incubation and magnetic beads handling steps as described above. Individually selectable temperature setting, mixing strength, speed and magnetic beads handling allow customization to various applications and conditions.

Many changes in the details, materials, and arrangement of parts and steps, herein described and illustrated, can be made by those skilled in the art in light of teachings contained hereinabove. It will be understood that certain features and sub-combinations are of utility and may be employed without reference to other features and sub combinations and are contemplated within the scope of the claims. Accordingly, it will be understood that the following claims are not to be limited to the embodiments disclosed herein and can include practices other than those specifically described, and are to be interpreted as broadly as allowed under the law. Additionally, not all steps listed in the various figures need be carried out in the specific order described.

We claim:

1. A vortex generator assembly for performing nucleic acid isolation, comprising:
    a sample holder comprising a body member forming a channel extending from a first end to an opposite second end of the sample holder, the sample holder further comprising a first plurality of wells for holding at least a fluid extending in a downwardly direction from a floor of the channel, each well having an interior volume; and
    a sample holder cover comprising a base member comprising a floor extending from a first end to an opposite end of the sample holder cover, a removable retention mechanism configured to securely retain the sample holder cover in the channel when the base member is inserted into the channel, and a second plurality of vibration rods extending in a downwardly direction from the floor of the base member into the interior volume of a corresponding one of the first plurality of wells when the base member is inserted into the channel.

2. The vortex generator assembly of claim 1, wherein the base member further comprises a plurality of cantilevers formed in the floor, and said second plurality of vibration rods are attached to said cantilevers so the second plurality of vibration rods may be vibrated to mix the at least a fluid in a corresponding well.

3. A vortex generator assembly for performing nucleic acid isolation, comprising:
   a sample holder comprising a body member forming a channel extending from a first end to an opposite second end of the sample holder, the sample holder further comprising a first plurality of wells for holding at least a fluid extending in a downwardly direction from a floor of the channel, each well having an interior volume; and
   a sample holder cover comprising a base member comprising a floor extending from a first end to an opposite end of the sample holder cover and a second plurality of vibration rods extending in a downwardly direction from the floor of the base member into the interior volume of a corresponding one of the first plurality of wells when the base member is inserted into the channel,
   wherein base member further comprises a plurality of cantilevers formed in the floor, and said second plurality of vibration rods are attached to said cantilevers so the second plurality of vibration rods may be vibrated to mix the at least a fluid in a corresponding well, and
   wherein said base member further comprises a plurality of tabs attached to the plurality of cantilevers extending in an upwardly direction from the floor, said tabs extending above a rim of the base member.

4. The vortex generator assembly of claim 1, wherein the first plurality of wells further comprises a lysis well proximate the first end of the body member, at least one wash well intermediate the first and second end, and an elution well proximate the second end of the body member.

5. The vortex generator assembly of claim 4, further comprising one or more additional wash wells.

6. The vortex generator assembly of claim 4, wherein the lysis well has a larger volume than the at least one wash well.

7. The vortex generator assembly of claim 4, wherein the elution well has a smaller volume than the at least one wash well.

8. The vortex generator assembly of claim 4, wherein the elution well has a conical cross-section.

9. A vortex generator assembly for performing nucleic acid isolation, comprising:
   a sample holder comprising a body member forming a channel extending from a first end to an opposite second end of the sample holder, the sample holder further comprising a first plurality of wells for holding at least a fluid extending in a downwardly direction from a floor of the channel, each well having an interior volume; and
   a sample holder cover comprising a base member comprising a floor extending from a first end to an opposite end of the sample holder cover and a second plurality of vibration rods extending in a downwardly direction from the floor of the base member into the interior volume of a corresponding one of the first plurality of wells when the base member is inserted into the channel,
   wherein at least one of the sample holder and the sample holder cover comprise a retention feature for enabling selective retention of the sample holder cover to the sample holder by a releasable gripping mechanism.

10. The vortex generator assembly of claim 1, wherein the first plurality of wells are linearly centered along an axis of symmetry of the body member between the first and second ends of the sample holder.

11. The vortex generator assembly of claim 1, wherein the vibration rods have an asymmetric cross section.

12. The vortex generator assembly of claim 3, wherein the first plurality of wells further comprises a lysis well proximate the first end of the body member, at least one wash well intermediate the first and second end, and an elution well proximate the second end of the body member.

13. The vortex generator assembly of claim 3, wherein at least one of the sample holder and the sample holder cover comprise a retention feature for enabling selective engagement of the sample holder by a releasable gripping mechanism.

14. The vortex generator assembly of claim 3, wherein the first plurality of wells are linearly centered along an axis of symmetry of the body member between the first and second ends of the sample holder.

15. The vortex generator assembly of claim 3, wherein the vibration rods have an asymmetric cross section.

16. The vortex generator assembly of claim 9, wherein the base member further comprises a plurality of cantilevers formed in the floor, and said second plurality of vibration rods are attached to said cantilevers so the second plurality of vibration rods may be vibrated to mix the at least a fluid in a corresponding well.

17. The vortex generator assembly of claim 9, wherein the first plurality of wells further comprises a lysis well proximate the first end of the body member, at least one wash well intermediate the first and second end, and an elution well proximate the second end of the body member.

18. The vortex generator assembly of claim 17, wherein the elution well has a conical cross-section.

19. The vortex generator assembly of claim 9, wherein the first plurality of wells are linearly centered along an axis of symmetry of the body member between the first and second ends of the sample holder.

20. The vortex generator assembly of claim 9, wherein the vibration rods have an asymmetric cross section.

* * * * *